US00PP19592P2

(12) United States Plant Patent
Delabroye

(10) Patent No.: US PP19,592 P2
(45) Date of Patent: Dec. 23, 2008

(54) *HEUCHERA* PLANT NAMED 'PINOT GRIS'

(50) Latin Name: *Heuchera*
Varietal Denomination: Pinot Gris

(76) Inventor: Sandrine Delabroye, Rue Roger Salengro 40, Hantay (FR), F-59496

( * ) Notice: Subject to any disclaimer, the term of this patent is extended or adjusted under 35 U.S.C. 154(b) by 0 days.

(21) Appl. No.: 12/008,928

(22) Filed: Jan. 15, 2008

(51) Int. Cl.
*A01H 5/00* (2006.01)

(52) U.S. Cl. ..... Plt./440

(58) Field of Classification Search ..... Plt./440, Plt./263.1
See application file for complete search history.

*Primary Examiner*—Annette H Para
(74) *Attorney, Agent, or Firm*—Penny J. Aguirre

(57) ABSTRACT

A new cultivar of hybrid *Heuchera* named 'Pinot Gris', characterized by its unique foliage with its orbicular shaped wavy leaves that emerge orange-yellow with a silver overlay in spring changing to a rosy grayed red in summer with increasing amount of silver overlay and dark rosy red veins. 'Pinot Gris' is further characterized by its compact and mounded plant habit, its tolerance to heat, humidity, and exposure to sunlight, and its hardiness in U.S.D.A Zones 4 to 9.

2 Drawing Sheets

Botanical classification: *Heuchera* hybrid.
Cultivar designation: 'Pinot Gris'.

CROSS REFERENCE TO A RELATED APPLICATION

This application is co-pending with U.S. Plant patent applications filed for sibling plants derived from the same cross in the inventor's breeding program that are entitled *Heuchera* Plant Named 'Pinot Noir' (U.S. Plant Pat. application Ser. No. 12/002,889), *Heuchera* Plant Named 'Encore' (U.S. Plant Pat. application Ser. No. 12/008,941) *Heuchera* Plant Named 'Pistache' (U.S. Plant Pat. application Ser. No. 12/008,927), *Heuchera* Plant Named 'Tiramisu' (U.S. Plant Pat. application Ser. No. 12/002,921), and *Heuchera* Plant Named 'Beaujolais' (U.S. Plant Pat. application Ser. No. 12/008,338).

BACKGROUND OF THE INVENTION

The present invention relates to a new and distinct cultivar of hybrid *Heuchera,* botanically known as a *Heuchera* of hybrid origin and is hereinafter referred to by the cultivar name 'Pinot Gris'.

'The new cultivar was derived from a controlled breeding program by the inventor in Hantay, France. The inventor made a cross in summer of 2005 between *Heuchera* 'Gloire d'Orleans' (not patented, syn. *Heuchera×brizoides* 'Gloire d'Orleans') as the male parent and *Heuchera×villosa* 'Caramel' (U.S. Plant Pat. No. 16,560) as the female parent. The goal of the breeding program was to obtain unique cultivars of *Heuchera* that combined the flowering habit of 'Gloire d'Orleans' with the vigor and unique foliage coloration of *Heuchera×villosa.* The inventor selected 'Pinot Gris' in 2006 as a single unique plant amongst the seedlings that resulted from the above cross.

Asexual reproduction of the new cultivar was first accomplished under direction of the inventor by in vitro propagation in Rijswijk, The Netherlands in winter of 2007. Asexual reproduction of the new cultivar by division and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Pinot Gris' as a new and unique cultivar of *Heuchera.*

1. 'Pinot Gris' exhibits unique foliage with leaves that emerge orange-yellow with a silver overlay in spring changing to a rosy grayed red in summer with increasing amount of silver overlay and dark rosy red veins.
2. 'Pinot Gris' exhibits orbicular shaped, wavy leaves.
3. 'Pinot Gris' exhibits a compact, mounded plant habit.
4. 'Pinot Gris' is tolerant to high heat and humidity and high light levels imparted by having *Heuchera×villosa* in its parentage.
5. 'Pinot Gris' is cold hardy at least in U.S.D.A. Zones 4 to 9.

The spring foliage of 'Pinot Gris' is similar to its female parent plant, 'Caramel', in however the foliage of 'Caramel' lacks a silver overlay and does not change to rosy red in summer. 'Pinot Gris' differs from its male parent, 'Gloire d'Orleans', in that 'Gloire d'Orleans' is a *×brizoides* hybrid with green foliage.

The closest comparison plants in overall leaf shape, habit, and performance are its sibling cultivars that differ in foliage coloration. 'Encore' is similar in having rose-colored foliage with a silver overlay, however, 'Encore' differs most significantly in lacking orange-yellow foliage in spring. Other sibling cultivars include; 'Pinot Noir' with dark purple-grey foliage, 'Pistache' with yellow-green foliage, 'Tiramisu' with foliage that is yellow-green with red mottling, and 'Beaujolais' with foliage that is burgundy red with a silver overlay.

BRIEF DESCRIPTION OF THE DRAWING

The accompanying colored photographs illustrate the overall appearance and distinct characteristics of the new

*Heuchera*. The photographs were taken in mid summer of plants six months in age as grown in a 2-liter container in The Netherlands.

The photograph on the first sheet provides a side view of the plant habit of 'Pinot Gris' and provides a view of both the summer foliage (center leaves) and spring foliage (outer leaves).

The photograph on the second sheet provides a close-up view of a summer leaf of 'Pinot Gris' in the foreground and a spring leaf in the background.

The colors in the photographs are as close as possible with the photographic and printing technology utilized. The color values cited in the detailed botanical description accurately describe the colors of the new *Heuchera*.

DETAILED BOTANICAL DESCRIPTION OF THE PLANT

The following is a detailed description of a six month-old plants of the new cultivar as grown in a 2-liter container outdoors in The Netherlands. Plants were grown under average day temperatures of 12° to 30° C. and average night temperatures of 5 to 16° C. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General Description:

*Plant habit.*—Compact, clump-forming, mounded, herbaceous perennial.

*Height and spread.*—Reaches a height of about 12.3 cm in height and about 24.5 cm in width.

*Hardiness.*—At least in U.S.D.A. Zones 4 to 9.

*Culture.*—Full sun to medium shade in moist, well-drained, fertile soils, tolerant to high heat and humidity as well as high light levels.

*Diseases and pests.*—Disease free in the conditions tested, no susceptibility or resistance to pests has been observed.

*Root description.*—Fibrous roots on woody rootstalks.

*Branching habit.*—Basal rosettes of leaves on petioles.

*Propagation.*—In vitro propagation is the preferred method, division are also possible.

*Root initiation.*—Roots appear in rooting media in 10 days at 20° C. in the laboratory without supplemental lighting.

*Root development.*—Rooted transplants from tissue culture fully develop in a 2.5 inch plug in about 20 days in a greenhouse with average temperatures of about 20° C. without supplemental lighting in The Netherlands.

*Growth rate.*—Moderate, grows about 5 cm per month in spring, with an average crop time of 20 weeks to develop in a 9 cm container.

Foliage Description:

*Leaf shape.*—Orbicular.

*Leaf division.*—Simple.

*Leaf base.*—Hastate, moderately overlapping.

*Leaf apex.*—Rounded with a very small acute tip 0.5 mm in length.

*Leaf venation.*—Primary palmate, secondary net-veined, conspicuous on upper surface, color on upper surface; 172A to 172B on summer leaves and 151C to 151D on spring leaves, color on lower surface 152D.

*Leaf margins.*—Lobed with an average number of 5 lobes, lobe margins crenate.

*Leaf attachment.*—Petiolate.

*Leaf arrangement.*—Basal rosettes.

*Leaf orientation.*—Held nearly horizontal to petiole, wavy.

*Leaf surface.*—Upper and lower surface sparsely covered with white hairs 0.7 mm in length and 155C in color.

*Leaf color.*—Upper surface in spring; 161A to 161C with overlay of 190B and veins and margins 151C to 151D, lower surface in spring; 178B to 178C to 181B, upper surface in summer; 177D with overlay of 190B and veins and margins 172A to 172B, lower surface in summer 59A to 184B.

*Leaf size.*—Average of 8.7 cm in length and 8.1 cm in width.

*Leaf quantity.*—Average of 40 per 3-liter container.

*Petioles size.*—Round, average of 9 cm in length and 2 mm in diameter, color is 152B tinged with 165A, surface is villose with abundant hairs about 1.5 mm in length and 155C in color.

*Stipules.*—None.

Flower and seed description: Flowering was been observed under the conditions grown for data collection, creamy white bell-shaped flowers typical of *Heuchera* should be expected under the right conditions for flowering, seed production has not been observed.

It is claimed:

1. A new and distinct cultivar of *Heuchera* plant named 'Pinot Gris' as herein illustrated and described.

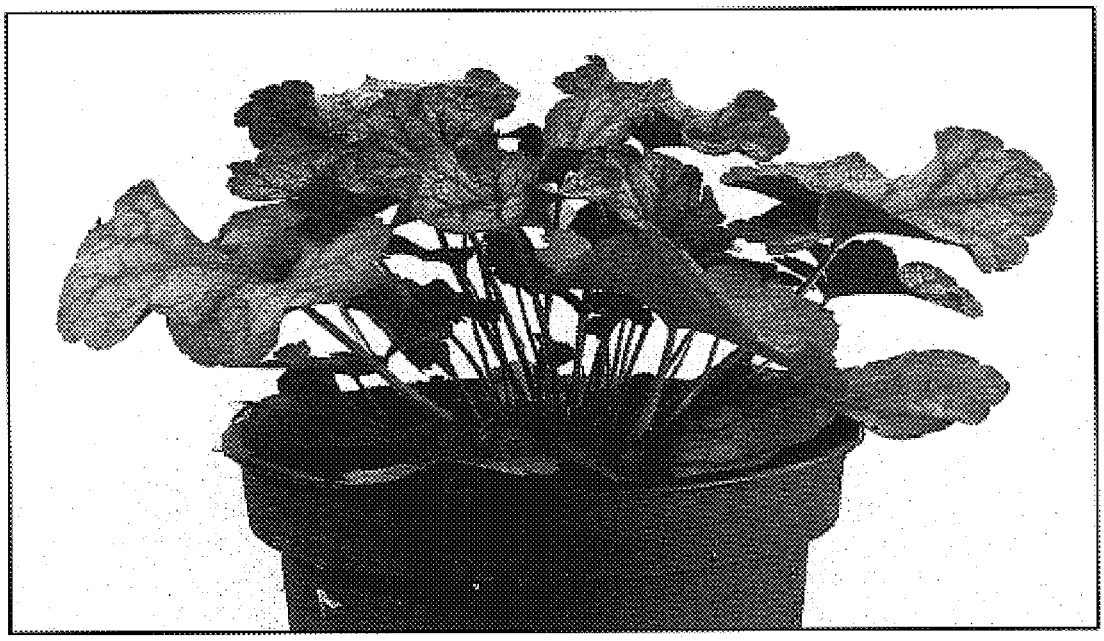

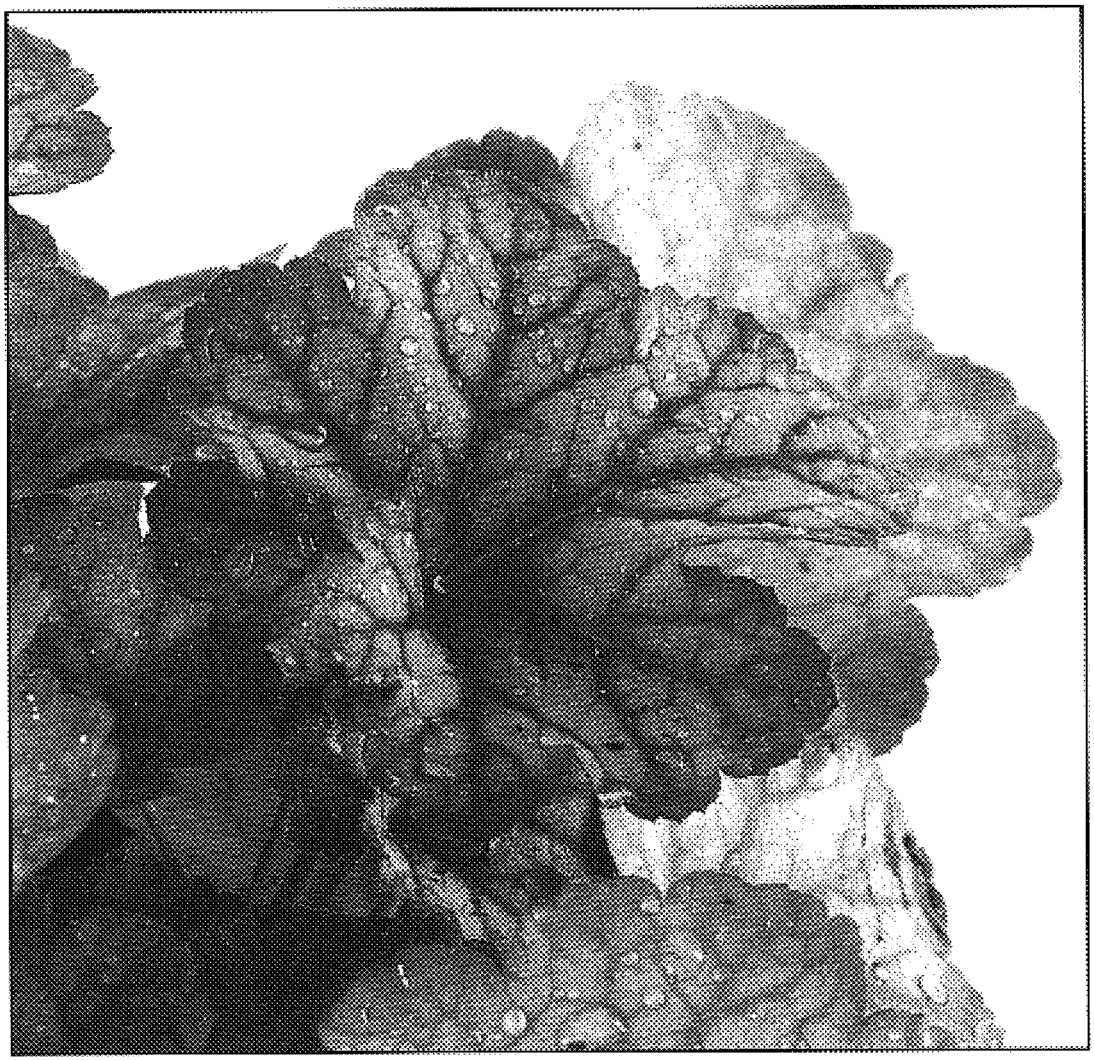

* * * * *